United States Patent [19]
Vecere

[11] Patent Number: 5,898,113
[45] Date of Patent: Apr. 27, 1999

[54] MULTI-PLY MATERIAL SEALED CONTAINER

[75] Inventor: William T. Vecere, Warren, Mich.

[73] Assignee: Bellaire Industries, Inc., Royal Oak, Mich.

[21] Appl. No.: 08/902,700

[22] Filed: Jul. 30, 1997

[51] Int. Cl.⁶ ....................................................... G01N 1/00
[52] U.S. Cl. ........................................ 73/864.62; 383/113
[58] Field of Search .......................... 73/864.51, 864.62, 73/864.63, 864.91, 23.31–23.33; 383/3, 41, 109, 904, 906, 113, 116; 137/561 A, 590, 592

[56] References Cited

U.S. PATENT DOCUMENTS

| | | |
|---|---|---|
| 3,357,632 | 12/1967 | Stanforth . |
| 4,700,531 | 10/1987 | Hsu et al. . |
| 4,718,778 | 1/1988 | Ichikawa . |
| 4,756,422 | 7/1988 | Kristen . |
| 5,129,813 | 7/1992 | Shepherd . |
| 5,147,071 | 9/1992 | Rutter et al. . |
| 5,218,874 | 6/1993 | Vecere . |
| 5,239,877 | 8/1993 | Suddath et al. . |
| 5,242,111 | 9/1993 | Nakomeczny et al. . |
| 5,250,042 | 10/1993 | Torgalkar et al. . |
| 5,438,884 | 8/1995 | Suddath . |

OTHER PUBLICATIONS

Technical Bulletin, Guide To Flexible Fabrics Protected With TEDLAR PVF Film For Awning And Sign Systems, Pub. DuPont Co. TD–37 Rev. Aug. 1990.
Technical Bulletin, "TEDLAR PVF Film" (no dates), Pub. DuPont Co.
Technical Bulletin, "Westlake PVDF Film made from KYNAR", (no dates), Pub. Westlake Plastics Company.

*Primary Examiner*—Robert Raevis
*Attorney, Agent, or Firm*—Young & Basile, PC

[57] ABSTRACT

An expandable sealed container is formed of first and second panels, each formed of at least first and second sheets. The first sheet of each of the panels is formed of a polyvinyl fluoride film and the second sheet is formed of a flexible vinyl. In one embodiment, one surface of the polyvinyl fluoride film is treated to receive an adhesive to adhesively join the polyvinyl fluoride sheet to the vinyl sheet. The opposed second surface is capable of receiving a heat seam to form a complete peripheral seal about the container. In one configuration, the polyvinyl fluoride film sheets of each pair of sheets are facing each other and receive the heat seam. Alternately, the vinyl layers are disposed innermost to receive the heat seam. Further, a polyvinyl fluoride film having both surfaces treated to receive an adhesive is adhesively joined to the outermost surface of the vinyl sheet. The heat seam is formed about the periphery of the vinyl sheets.

8 Claims, 1 Drawing Sheet

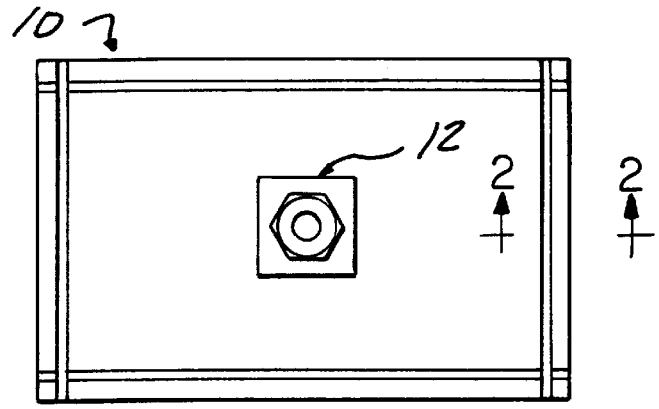
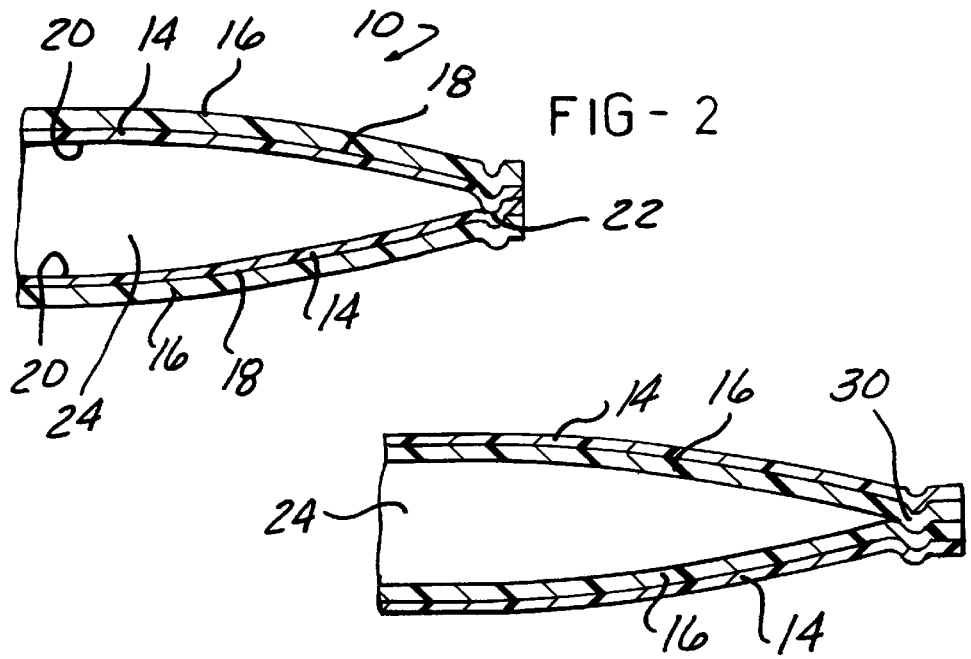

MULTI-PLY MATERIAL SEALED CONTAINER

BACKGROUND OF THE INVENTION

1. Field of The Invention

The present invention relates, in general, to sealed, expandable containers and, more specifically, to gas containers formed of multiple sheet layers.

2. Description of the Art

Expandable sealed containers or bags are employed in numerous applications, such as for collecting and temporarily storing gas emissions for motor vehicles before the collected emissions are analyzed by test equipment. Such containers are expandable to a constant volume to collect a known quantity of gaseous emissions.

Such expandable containers typically include a fitting sealingly mounted through one sidewall which is connectable to an external gas source and discharge device for receiving external gases and for discharging such gases from the container. The fitting directs the gas into the container for storage as well as allowing the stored gas to be completely evacuated from the container. The fitting and the sealed container are typically made of an inert material, such as a fluorinated carbon plastic sold under the registered trademarks TEFLON and TEDLAR.

In constructing such an expandable container, single thickness or ply sheets are overlaid on each other and sealingly connected at their peripheral edges by a conventional heat seam or seal.

TEDLAR polyvinyl fluoride film (PVF) is ideally suited for a number of applications due to its resistance to many chemicals, ultraviolet radiation, etc. In expandable container applications, polyvinyl fluoride film is used in a surface characteristic allowing heat sealing. Other formulations of TEDLAR polyvinyl fluoride film cannot be heat sealed. TEDLAR polyvinyl fluoride film is available in at least two formulations labeled "A" TEDLAR and "B" TEDLAR. "B" TEDLAR is treated on both side surfaces to enable adhesive to adhere to the sheet thereby permitting the bonding of the polyvinyl fluoride film or sheet to another sheet or material layer. For example, TEDLAR PVF film is laminated by an adhesive to flexible and reinforced vinyl fabrics for a number of indoor and outdoor applications including signs, awnings, and protective covers. The fabric or filaments are typically disposed inside of the PVF material layers to provide strength and stability to the material stock. The PVF film is disposed outermost over the vinyl fabric for ultraviolet protection and easy cleanup.

However, "B" TEDLAR which is treated on both surfaces for receiving adhesive is not heat sealable thereby preventing the use of this material in expandable bags formed of multiple sheets which are heat sealed at their peripheral edges. "A" TEDLAR PVF film has only one surface treated for receiving an adhesive. The other surface is "strippable" so as to be heat sealable to like "A" TEDLAR PVF films. Thus, it would be desirable to provide a sealed, expandable container which makes use of the advantages of a multiple ply stack of polyvinyl fluoride film and other materials while at the same time being easily heat sealable to form a sealed interior container. It would also be desirable to provide a sealed container formed of multiple ply sheets in which at least one sheet is a polyvinyl fluoride film and the at least one other sheet is a flexible vinyl.

In certain applications, the noise generated by the crinkling of the expandable container as it expands and contracts is objectional. Thus, it would be desirable to provide an expandable sealed container which is constructed to generate less objectional noise during expansion and contraction of the container.

SUMMARY OF THE INVENTION

The present invention is an expandable sealed container suitable for receiving, storing, and discharging gas.

In one embodiment, the container comprises first and second flexible plastic panels, each of the first and second panels being formed of at least first and second separate sheets disposed in overlapping relationship with each other. The first sheet of each of the first and second panels is formed of polyvinyl fluoride. The second sheet of each of the first and second panels is formed of a flexible vinyl material.

The first and second sheets of each of the first and second panels are oriented so as to enable a heat seam to be formed completely about the peripheral edges of the first and second panels to form a hollow, expandable, sealed chamber between the innermost facing surfaces of the first and second panels. An adhesive layer is interposed between the overlapping surfaces of the first and second sheets of each of the first and second panels to adhesively join the first and second sheets of each of the first and second panels together.

In one embodiment, the first sheet of each of the first and second panels is formed of a polyvinyl fluoride material having one surface treated to receive an adhesive and a second surface capable of being heat seamed to another sheet. In this embodiment, the first sheets of each of the first and second panels are disposed facing each other and the second sheets of vinyl material are disposed outermost of the first sheets. A heat seam is formed about the peripheral edges of all of the first and second sheets of each of the first and second panels in this embodiment.

In another embodiment, the second sheets of vinyl material are disposed innermost facing each other. The first sheets of polyvinyl fluoride material are disposed outermost of the second sheets of vinyl material and are adhesively joined to the second vinyl sheets. In this embodiment the heat seam is formed only between the inner vinyl sheets.

In another embodiment, the first sheet is formed of polyvinyl fluoride material having both opposed surfaces treated to receive an adhesive. The second sheet is formed of a flexible vinyl. An adhesive fixedly joins one surface of the first sheet to one surface of the second sheet of each of the first and second panels. The heat seam formed about the peripheral edges of the second sheets of vinyl material of the first and second panels.

Alternatively, KYNAR polyvinylidene fluoride resin film may be substituted for the PVF film in all of the above-described embodiments of the sealed container.

The sealed container of the present invention uniquely takes advantage of the characteristics provided by two diverse material layers, such as a polyvinyl fluoride layer and a flexible vinyl layer or polyvinylidene fluoride film and vinyl. Depending upon the orientation of the polyvinyl fluoride film and vinyl layers in forming the sealed container, the polyvinyl fluoride film provides a gas impervious surface surrounding the gas expansible chamber with the outer vinyl layer providing sound deadening as well as strength and durability to the container. Alternately, disposing the polyvinyl fluoride layers outermost provides ultraviolet protection and contaminant resistance to the interior vinyl layers.

In all embodiments of the sealed container of the present invention, the sheets forming each sidewall or panel of the container are formed of diverse materials which are selected and arranged to enable a heat seam to be easily formed about the complete periphery of at least certain or all of the material layers to form an expansible sealed chamber within the container.

BRIEF DESCRIPTION OF THE DRAWINGS

The various features, advantages and other uses of the present invention will become more apparent by referring to the following detailed description and drawing in which:

FIG. 1 is a plan view of a expandable, sealed container constructed in accordance with the teachings of the present invention;

FIG. 2 is a cross-sectional view, generally taken along line 2—2 in FIG. 1, and showing the multiple layer construction of the expandable container depicted in FIG. 1;

FIG. 3 is a cross-sectional view, generally similar to FIG. 2, but showing an alternate embodiment of the container; and FIG. 4 is a cross-sectional view, generally similar to FIG. 2, but showing yet another embodiment of the container.

DESCRIPTION OF THE PREFERRED EMBODIMENTS

Refer now to the drawing, and to FIGS. 1 and 2 in particular, there is depicted an expandable container 10 which is connectable via a fitting 12 mounted on the container 10 to an external conduit, not shown, for collecting, temporarily storing and discharging gaseous fluids to and from the container 10. In a particular embodiment, the container 10 is usable as a gas emission sample container which is used to collect and temporarily store gas emissions from a motor vehicle prior for evacuation of the stored gas emissions for subsequent analysis.

The container 10 is a sealed enclosure of any shape, such as rectangular, square, circular, etc. It will be understood that the rectangular shape for the container 10 shown in FIG. 1 is by way of example only. Further, depending upon the application, the container 10 may be provided in different sizes.

The sealed container 10, in one embodiment, is formed of first and second pairs of flexible sheets, with each pair of sheets forming one panel or sidewall of the container 10. In the embodiment shown in FIG. 2, each of the first and second pairs of sheets is formed of a first polyvinyl fluoride sheet 14 and a second flexible vinyl sheet 16. By example only, the first sheet 14 is one to two mils in thickness and the second sheet 16 is 3 mils in thickness.

In this embodiment, the first layer 14 is formed of "A" TEDLAR polyvinyl fluoride film. This film has one surface 18 treated for receiving an adhesive, not shown, to join the first sheet 14 to the second sheet 16. The opposite surface 20 of the first layer 14 is strippable or heat sealable.

In constructing the container 10 in the embodiment shown in FIG. 2, the first and second pairs of sheets are inverted from each other such that the first sheets 14 of each first and second pairs of sheets are facing each other. This places the strippable or heat sealable surfaces 20 of each of the first sheets 14 in registry with each other at their peripheral edges so as to enable a heat seal 22 to be formed around the complete outer periphery of the layers 14 to form a sealed interior chamber 24 within the container 10.

This arrangement for the sealed container 10 combines the advantages of the polyvinyl fluoride film sheet 14 and the outermost vinyl sheet 16. The vinyl provides strength and stability as well as deadening any noise which may be generated through crinkling of the inner first sheet 14 during expansion and contraction of the container 10. The inner first sheet 14 provides a gas impervious and inert layer adjacent the gas contained within the interior chamber 24.

A second embodiment of the container 10, shown in FIG. 3, is substantially identical to the embodiment described above and shown in FIG. 2, except that the orientation of the sheets 14 and 16 in each of the first and second pairs of sheets are reversed from that shown in FIG. 2. In this embodiment, the flexible vinyl sheet 16 is disposed innermost in facing registry with the vinyl layer 16 of the opposite pair of sheets. The "A" TEDLAR polyvinyl fluoride film sheets 14 are disposed outermost and adhesively joined to the corresponding vinyl sheet 16. In this embodiment, a heat seam or seal 30 is formed about the periphery of the vinyl sheets 16. A heat seam through the outer PVF film sheets 14 is not necessary or possible, however the sheets 14 are adhesively joined to the adjacent vinyl layer 16.

FIG. 4 depicts another embodiment of the container 10 of the present invention. In this embodiment, the pairs of sheets forming the container 10 are formed of a "B" TEDLAR PVF sheet 32 and a flexible vinyl sheet 34. The flexible vinyl layers 34 are disposed in facing registry so as to receive a peripheral heat seam 36 thereabout, thereby forming a sealed expansible chamber 38 between the opposed, non-sealed portions of the vinyl sheets 34. The PVF film sheets 32 are disposed outermost and adhesively joined to the adjacent vinyl layer 34. Since "B" TEDLAR is not strippable or heat seamable, the heat seam 36 is formed solely between the two vinyl sheets 34 thereby forming the desired sealed chamber 38 within the container 10.

Any suitable fitting may be mounted in the container 10 through aligned apertures formed in one pair of sheets 14 and 16 in the embodiment shown in FIGS. 2 and 3 or one pair of sheets 32 and 34 in the embodiment shown in FIG. 4. Any fitting structure and mounting arrangement, such as those described and shown in U.S. Pat. Nos. 5,074,155; 5,239,877; and 5,438,884 may be employed. The contents of these patents, pertaining to the construction, mounting, and operation of the fittings, are incorporated herein by reference. It will also be understood that any other fittings suitable for use in an expansible container may also be mounted in the container at any location, other than the generally central location shown in FIG. 1.

By way of example only, the fitting 12 shown in FIGS. 1 and 4 includes an elongated, threaded shaft 40 having a hex head 42 at one end. A bore 44 is formed in the shaft for receiving a flexible conduit, not shown. A washer 46, such as a nylon washer, and a gasket 48 are stacked between the head 42 and the outer sheet 32 of the container 10. A similar gasket 50 is disposed adjacent the inner surface of the inner sheet 34. A threaded nut 52 is disposed within the interior chamber 38 of the container 10 and threaded onto the end of the shaft 40 to secure all of the fitting components together. As a substitute for the "A" TEDLAR and "B" TEDLAR polyvinyl fluoride film sheets described above, KYNAR polyvinylidene fluoride resin sheets may also be employed as the gas impervious and inert layer on each sidewall of the container 10 of the present invention. Such sheets have properties similar to the PVF film in that one or both surfaces of the polyvinylidene fluoride sheet may be surface treated for receiving an adhesive. Such surfaces may also be treated or are adaptable for receiving a heat seam.

In summary, there has been disclosed a unique sealed container which enables a multi-ply sheet stack, to be heat sealed at their peripheral edges to form a sealed, expansible chamber within the container while providing the advantages of two diverse materials forming each container sidewall.

What is claimed is:

1. A gas storage container for receiving, storing and discharging gas, the container comprising:

first and second flexible plastic panels, each being formed of at least first and second separate sheets disposed in overlapping relationship with each other;

the first sheet of each of the first and second panels formed of one of polyvinyl fluoride and polyvinylidene fluoride;

the first sheet having opposed first and second surfaces, with at least the first surface treated to receive an adhesive and being non-heat seamable;

the second sheet of each of the first and second panels having opposed surfaces and formed of a flexible vinyl material;

an adhesive interposed between the overlapping surfaces of the first surface of the first sheet and the second sheet of each of the first and second panels to adhesively join the first and second sheets of each of the first and second panels together; and the first and second sheets of each of the first and second panels oriented so as to enable a heat seam to be formed completely about the peripheral edges of overlapping, non-adhesive coated surfaces of at least one other of the first and second sheets of the first and second panels to form a hollow, expandable, sealed chamber between the innermost, non-sealed portions of the first and second panels.

2. The apparatus of claim 1 wherein:

the second surface of the first sheet of each of the first and second panels is capable of heat seaming to another one of the first and second sheets.

3. The apparatus of claim 2 wherein:

the second surfaces of the first sheets of each of the first and second panels are disposed facing each other; and the second sheets are disposed outermost of the first sheets in each of the first and second panels.

4. The apparatus of claim 3 wherein a heat seam is formed in the peripheral edges of the second surfaces of the first sheets of the first and second panels.

5. The apparatus of claim 2 wherein:

the second sheets are disposed facing each other; and the first sheets are disposed outermost of the second sheets.

6. The apparatus of claim 5 wherein:

a heat seam is formed in the peripheral edges of opposed surfaces of the second sheets of the first and second panels.

7. The apparatus of claim 1 wherein:

the first sheet has both first and second surfaces treated to receive an adhesive and being non-heat seamable; and the first sheets are disposed outermost of the second sheets in each of the first and second panels.

8. The apparatus of claim 7 wherein a heat seam is formed in the peripheral edges of opposed surfaces of the second sheets of the first and second panels.

* * * * *